(12) United States Patent
Jaillet

(10) Patent No.: US 6,443,977 B1
(45) Date of Patent: Sep. 3, 2002

(54) APPARATUS AND METHOD FOR CHANGING CRITICAL BRAIN ACTIVITY USING LIGHT AND SOUND

(76) Inventor: Peter D. Jaillet, 4212 Harvest Hill Ct., Carrollton, TX (US) 75010

( * ) Notice: Subject to any disclaimer, the term of this patent is extended or adjusted under 35 U.S.C. 154(b) by 0 days.

(21) Appl. No.: 09/545,052

(22) Filed: Apr. 7, 2000

Related U.S. Application Data

(63) Continuation-in-part of application No. 09/201,093, filed on Nov. 30, 1998, now Pat. No. 6,299,632.

(51) Int. Cl.[7] ................................................. A61N 5/06
(52) U.S. Cl. ............................................ 607/88; 600/27
(58) Field of Search .............................. 667/88, 90, 91; 600/26, 27, 28, 544, 545

(56) References Cited

U.S. PATENT DOCUMENTS

| | | | | | |
|---|---|---|---|---|---|
| 5,507,716 | A | * | 4/1996 | LaBerge et al. | 600/27 |
| 5,562,719 | A | * | 10/1996 | Lopez-Claros | 607/88 |
| 6,123,661 | A | * | 9/2000 | Fukushima et al. | 600/27 |
| 6,299,632 | B1 | * | 10/2001 | Jaillet | 607/88 |

\* cited by examiner

Primary Examiner—Rosiland S. Kearney
(74) Attorney, Agent, or Firm—Edwin S. Flores; Sanford E. Warren, Jr.; Gardere Wynne Sewell LLP

(57) ABSTRACT

An apparatus and method is disclosed for selectively stimulating cortical brain activity of a patient with hemispheric brain differences using light and/or sound includes exposing the patient to one or more lights (12) placed in close proximity to a patient's eyes (20, 30) wherein the one or more of lights (12) selectively stimulate the non-dominant eye (30) connected to the non-dominant cerebral hemisphere.

27 Claims, 5 Drawing Sheets

APPARATUS AND METHOD FOR CHANGING CRITICAL BRAIN ACTIVITY USING LIGHT AND SOUND

This application claims priority of U.S. patent application Ser. No. 09/201,093, filed Nov. 30, 1998, U.S. Pat. No. 6,299,632.

TECHNICAL FIELD OF THE INVENTION

The present invention relates to the field of critical brain stimulation, and more particularly, to an apparatus and method for the treatment of neural diseases through the controlled, targeted use of light and/or sound depending on the underlying physiologic pathology of a patient.

BACKGROUND OF THE INVENTION

Without limiting the scope of the invention, its background is described in connection with the use of light therapy to stimulate cerebral plasticity across hemispheres, as an example.

Light has been shown to effect the stability of a person's energy, mood, sleep, concentration and the regulation of a person's circadian rhythms. Light deprivation, for example, has been shown to cause fatigue, irritability, anxiety, weight gain, social withdrawal and a lack of alertness.

The human brain produces detectable signals that vary in strength and frequency over time. These signals are detectable as electromagnetic waves, and vary from one part of the brain to another and may, in fact, vary over time. Electromagnetic waves with different frequencies are associated with different moods and mental abilities.

It is generally believed that a person afflicted with a sleeping disorder has problems generating a delta rhythm. In contrast, people who have difficulties learning or display behavioral problems that affect learning, have problems associated with abnormalities of the alpha rhythm. These rhythms have been found to be regulated by brain biochemistry.

The use of light therapy, unlike drug therapy, has been used to treat patients that have been afflicted with a seasonal affective disorder. U.S. Pat. No. 5,562,719 to Lopez-Claros describes one such method for treating seasonal affective disorders that relies on preferential light stimulation in a hemifield pattern only affecting one quadrant or 50% of the non-dominant cerebral hemisphere. Seasonal affective disorder is a condition that affects from 5–20% of the population in areas with decreased year time light levels, such as the Northern Hemisphere. A common treatment for seasonal affective disorders is the use of lamps or light boxes that provide between 2,500 to 10,000 lux illumination in a hemifield pattern only affecting the inferior quadrant or 50% of the non-dominant cerebral hemisphere. The use of level illumination is an attempt to stimulate summer-like light levels. The Lopez-Claros patent is directed to the stimulation of one cerebral hemisphere to a greater degree than the other, thereby treating seasonal affective disorder by preferential light treatment. The Lopez-Claros invention, however, stimulates only one quadrant of the optical axis or 50% in both eyes thereby precluding its use in the stimulation of a hemisphere wholely.

As apparatus and method for treating an individual by electroencephalographic disentrainment feedback is the focus of U.S. Pat. No. 5,365,939 issued to Ochs. Electroencephalographic disentrainment feedback involves measuring a patient's brain waves, and based on those brain waves, generating impulses that disrupt brain waves by "disentraining" brain waves that are "entrained" or entrenched in the brain. By "disentraining" the entrenched brain waves, a patient's sub-optimal posttraumatic neural functioning is restored. The apparatus, however, requires the supervision of a doctor, as people with hypersensitivity may require that treatment be immediately stopped. The increased supervision makes the cost of use very great and eliminates its portability.

A slight variation from the Ochs patent, is U.S. Pat. No. 5,036,858 issued to Carter and Russell, that involves using two frequencies, with a slight frequency differential between the two frequencies, to change a patient's brain waves. The patient's brain waves are also measured, and based on these measurements, disruptive brain impulses are generated that disrupt the patient's brain waves in a constant feedback mechanism.

SUMMARY OF THE INVENTION

The invention disclosed herein is an apparatus for selectively stimulating target regions of the cerebral hemisphere using a controlled light and sound generating apparatus. The present invention helps address the present need for an apparatus and method that enhances the innate abilities of individuals with limbic disorders.

Also needed is an apparatus and method that is simple to use, inexpensive and portable, thereby providing greater distribution to those most in need of treatment. One example of individuals who may benefit the most from an inexpensive, simple to use device that increases learning abilities are patients and individuals in poor, urban, inner cities and in rural areas. More specifically, what is needed is a simple, inexpensive device that may be used by, e.g., elementary and secondary school children whose parent, or guardian, can not afford expensive drug treatments requiring medical supervision. Others that may benefit from such an apparatus and method are athletes, business people, and academicians.

In one embodiment the apparatus of the present invention is a device that covers the patient's eyes, such as a pair of sunglasses. Other devices may use similar technology in order to enhance ones ability to mentally focus. These devices include sports helmets that are used to protect players' craniums and may be integrated into the protective head gear, e.g., football, hockey, baseball, racing car, motorcycle and bicycle helmets.

Another application of the technology is with computer monitors and televisions. This embodiment encompasses one or more oscillating lights set-up in a proscribed manner on a person's computer monitor. The light pattern of the present invention may be displayed in a subliminal alternating checkerboard pattern that would be set to the individual user. In one embodiment, the light will stimulate the non-dominant cerebral hemisphere greater than the dominant cerebral hemisphere. In this version, the non-dominant cerebral hemisphere is stimulated to a greater degree than the dominant cerebral hemisphere. It is the coordinated stimulation of the non-dominant hemisphere that helps create a balance of integration of excitatory post synaptic potentials (EPSP).

The apparatus for selectively stimulating the non-dominant cerebral includes a surface placed in close proximity to a patient's eyes and one or more lights disposed on the surface. The one or more lights stimulate the eye connected to the non-dominant cerebral hemisphere to a greater extent than the eye connected to the dominant cerebral hemisphere at a rate of approximately, e.g., 60/40. By overstimulating the non-dominant hemisphere there is an increase in the patient's ability to maintain a heighten mental status, and in turn sets up for a globality of increased muscular activity.

Alternatively, the surface may be sleeping goggles. In yet another embodiment of the present invention, the glasses reflect light from a source next to the eye (light is reflected from the glass surface) into the patient's eyes.

The types of light that are used with the apparatus and method of the present invention may include white light, plane polarized light, or light that varies in color. The timing and intensity of the light may be controlled by a microcontroller or by an operator.

BRIEF DESCRIPTION OF THE DRAWINGS

For a more complete understanding of the features and advantages of the present invention, reference is now made to the detailed description of the invention along with the accompanying drawing in which corresponding numerals in the different figures refer to corresponding parts and, in which.

DETAILED DESCRIPTION OF THE INVENTION

Figure 1:
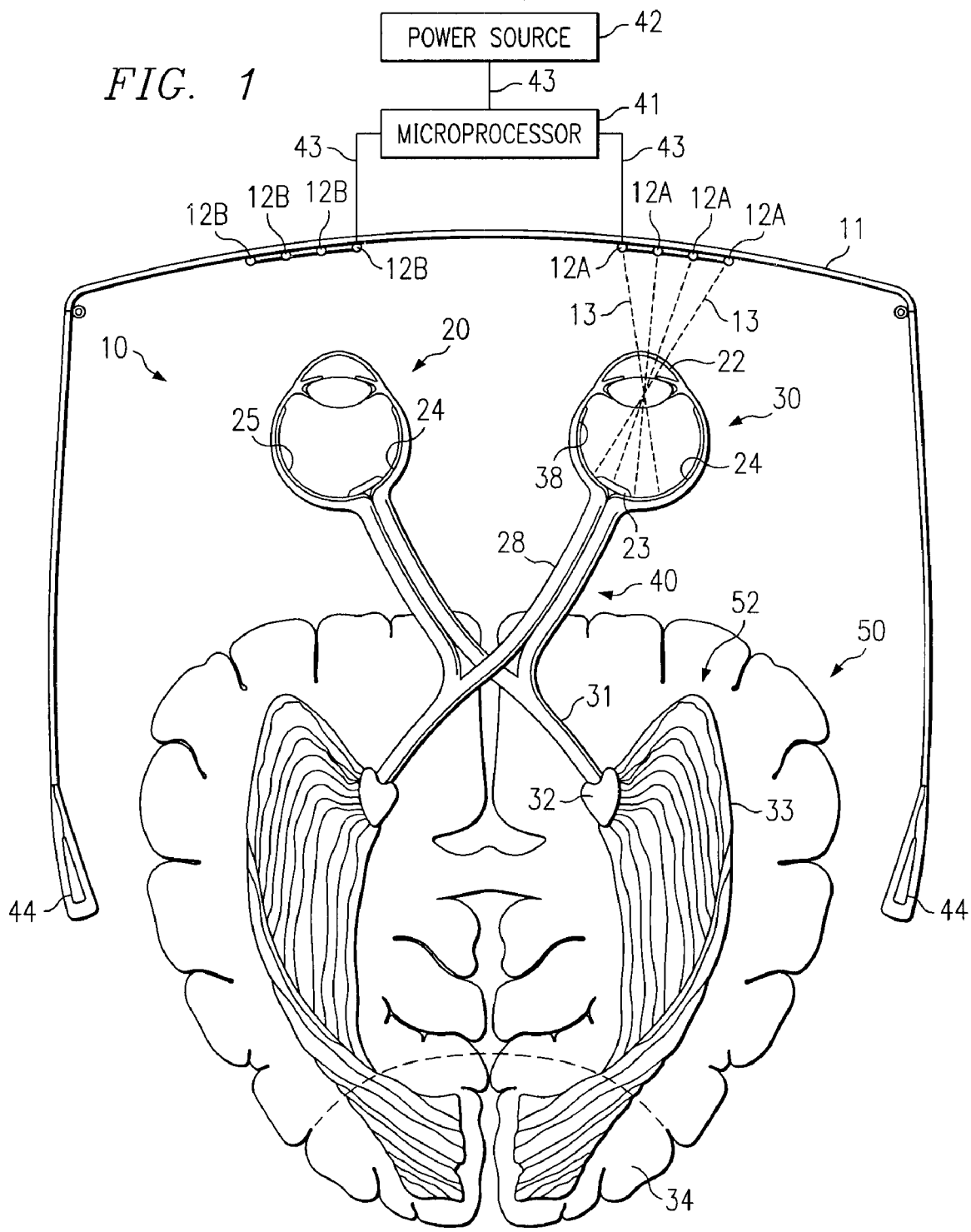
FIG. 1 is a presentation of the neural anatomy of the optical system and the relation of the visual fields.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention. The present invention has been developed based on empirical data obtained from patients. The underlying physiologic basis of the results, as disclosed hereinbelow, in now way should limit the scope of the invention.

The structures involved in the limbic system are the ventral mesencephalic tegmental mesolimbic neuronal pools called A10, which project into the amygdala, ventral putamen, ventral caudate, cingulate and the hippocampus. Presently, the only physical-clinical way to understand the integrity of a person's limbic reality is to conduct an accurate clinical history and to assess the function of the A10 cells. When A10 cells fire they produce dopamine, which is important of the survivability of the ventral neostriatum.

When mesencephalic A10 cells fire, they stimulate ventral neostriatal inhibition of pallidal inhibition of the motor thalamus. The stimulation of the ventral neostriatum allows the motor cells of the thalamus to reach threshold and fire the somesthetic strips 3,1,2, of the post-central gyrus, which in turn drive the primary, supplementary, and premotor strips 3,1,2, of the post-central gyrus. The stimulation of premotor strips 3,1,2, of the post-central gyrus, in turn, drive the primary, supplementary, and premotor strips of the precentral gyrus all 4, 4s, and 6. The consequence of this chain of neuro-stimulatory events is that, as a result of motor activity, these motor cells act in concert with emotional events.

When something in the environment evokes an emotional response, cells in the cerebellum fire before cells in the cortex. When cells fire in the cerebellum, these cells in turn fire monosynaptically to the A10 cells and to the pontine epinergic cells (Locus cerulcus A2, A4, and the sub cerulcus A1, A3, A5, A7). It is the motor event, therefore, that causes an emotional event to fire cells at the A10 loci.

It is based on this series of observations, in conjunction with the results demonstrated herein using the present invention, that it is now recognized that the controlled activation of the A10 cells allows a person to smile at something cute and cuddly, to laugh outwardly at a joke, etc. There are large postsynaptic pools from the A10 cells within the amygdala and the anterior cingulum. When cells in the amygdala and anterior cingulum are appropriately stimulated, they cause cells in the ventral neostriatum to fire, which in turn inhibit the release of the substantia nigra pars reticulatas and the globus pallidus pars intemus. The release of inhibition by the substantia nigra, pars reticulatas and the globus pallidus pars intemus releases the motor thalamus from inhibition resulting in a motor event.

Therefore, an overactive mesolimbic system may produce non-ballistic motoric activities without blepharospasm and with or without pupillary plasticity. It has been observed that an overactive mesolimbic system is a consequence of amygdala and cingulum activation of the neostriatum. Individuals with an overactive mesolimbic system are very spontaneous in regards to their motoric control. These patients tend to be very sarcastic and speak without thinking and potentially regret what they just said. For example, they may laugh at a funeral. These patients are also within the segment of the population that experience road rage with the concomitant motoric expression visualized by adjacent motorists as "flipping the bird" or screaming obscenities. A sub-segment of these patients also tend to present with angulations and dystonias of the left upper extremity due to aberrancies in right limbic expression with a probability of wind-down with specific basal ganglionic degeneration in the right cerebral cortex. It should be noted, however, that not all overactive mesolimbic patients experience any of these motoric overindulgences.

An underactive mesolimbic system may result in decreased amygdalal activation, which may decrease the neostriatal inhibition of the substantia nigra pars reticulatas and the globus pallidus pars intemus resulting in a shift towards K+equilibrium potential of the motor neurons of the thalamus. The result may be a loss of facial expression to the left side of the face.

A major problem in schools throughout the country is poor performance and discipline problems, caused in part by the learning disabilities of students. It has been estimated that at least 40 million Americans exhibit some symptoms of dyslexia, including up to 20% of all students. The results obtained using the non-invasive, non-pharmaceutical therapeutic treatment disclosed herein provide a radical new alternative for treating learning disabilities and other limbic disorders.

Learning begins at birth and involves the development of the brain hemispheres driven by the ability to perceive one's environment through the sensory system, i.e., touch, sound, smell, taste and vision. Children will thrive when they receive the proper sensory inputs and when signal pathways in the brain develop correctly. A lack of proper sensory inputs or incomplete development results in poor cognitive capability that manifests itself in poor learning skills. It is a major cause of ADD, ADHD and dyslexia.

The apparatus and method disclosed herein, named, EYELIGHTS, may be used for reconfiguring or redirecting nervous impulses to treat the symptoms of dyslexia, Attention Deficit Disorder (ADD) and Attention Deficit Hyperactive Disorder (ADHD). The symptoms of these diseases may be minimized or eliminated in many students, as demonstrated hereinbelow, and possibly in the general population. All the studies disclosed herein were conducted in a doctor-patient relationship under controlled conditions after having obtained full consent from the participants.

The problem of learning disabilities is a plague on US schools. For example, the "Attention Deficit Disorder" page in the "www.ONHEALTH.com" web site, assessable through "www.SNAP.com", states that as many as 20% of all school children are affected with ADD and ADHD. While many more boys are diagnosed with the problem, they state that it is becoming clear that ADD also affects many girls. Their difficulty lies mostly in inattention without hyperactivity as with boys and so the diagnosis may be overlooked. It is generally known in the art that common symptoms in these disease conditions include:

1) Habitual failure to pay attention;
2) Difficulties with school work;
3) Excessive distractability;
4) An inability to organize, even with activities that are enjoyed;
5) Difficulty following instructions and repeated failure to complete projects;
6) Impulsiveness;
7) Hyperactivity—fidgeting and running about; and
8) Excessive talking and frequent interrupting.

Dr. Harold Levinson, a widely published and reknowned expert on dyslexia, hosts a world wide web page at "dyslexiaonline.com". At this site Dr. Levinson states that over 40 million children and adults have symptoms of dyslexia. One of the most striking aspects of Dr. Levinson's research is the fact that over 78,000 visits have been made to the site since September 1998, approximately 11,000 visits per month, looking for help or information.

A very important feature of the present invention has been the ability, to demonstrate an improvement in the cognitive capability of a participant, e.g., students, through the use of light stimulation to the non-dominant hemisphere of the participant's brain. The results demonstrate that the apparatus and method of the invention provide a unique therapeutic benefit to the participants as shown by an improvement of cognitive skills.

The results disclosed herein also demonstrate a reduction or almost complete elimination of the symptoms of ADD, ADHD and dyslexia in participants at the elementary school level. The method also provides a means of determining the mechanism for the effect that heretofore would have required extensive invasive procedures on test subjects. The physiologic mechanism uncovered using the present invention involves the relationship that exists between physiological blind spot mapping (PBSI) and Caldwell's Visual Evoked Potentials (VEP). The invention was used to demonstrate the effectiveness of VEP in the diagnosis and treatment of ADD, ADHD and dyslexia.

Building on the knowledge base as the foundation for commercialization of the therapy and supporting hardware, the apparatus and methods disclosed herein may be used in a wide variety of applications. Such treatments include commercial applications through learning centers, optometrists, neurologist, kinesiologists, psychologist and others with the scientific and medical background to perform the diagnostic testing and manage the necessary treatment.

Hemispheric dominance is potentially a source of many learning problems. Hemispheric dominance is driven by the development of the visual system. Vision is one of the first systems to develop in young child, therefore, the visual system is the most important input systems in the development of the neuraxis. The development of an infant's eyes, e.g., is an indication of the impact of integration of midline brainstem nuclei upon the muscle development or control systems of the eyes.

As the development of the visual axis occurs, a corresponding development of the erector spinae musculature is observed during development. In this event, the child begins holding its head up, and progresses to sitting up, crawling, and finally standing up prior to walking. The visual system input toward the development of physical strength and muscle control are based primarily on thalamocorticocerebellar feedback loops. Therefore, visual stimulation and the concomitant development of the thalamocorticocerebellar brain centers may dictate the development of the brain. As the nervous system develops after birth, a noticeable disparity begins to develop in the midline structures of the child's visual system. Once midline development occurs, one of the hemispheres of the brain begins to become dominant.

The development of the midline structures occurs such that the brainstem nuclei that first develop will be those that are most medial, viz., cranial nerves 3, 4, 6, and 12. The first three allow for proper motoric interaction of visual development, e.g., the coordinated movement of the eyes.

The 12th nerve allows for proper development of the tongue musculature that, at birth, constitutes the sucking reflex and later, articulation. The coordinated movement of the tongue allows for proper speech development. To further understand the influence of the midline development it is necessary to understand that it is the concerted effort of the body to maintain homeostasis. When midline muscles develop, Aintegration takes place into the fastigeal nucleus of the cerebellum. The fastigeal nucleus of the cerebellum is involved in a closed loop of neuronal circuitry. Movement of the eyes, e.g., excites the midline nuclei 3, 4 and 6, through the muscles that they innervate about the eye, causing excitatory barrages to occur in the area acoustics. These barrages in turn excite the fastigeal nucleus in the cerebellum and increase the muscle tone of the multifidus and the intertransversaria muscles (erector spinae muscles). These neural and muscular events cause tectal spinal excitation, leading to the approximation of the facet joints of the cervical spine. These facet joints are full of mechanoreceptors that again send information to the cerebellum as to the position of the individual's head. Cerebellar information is then transferred to the cortex for motoric reactions to the stimulus.

When aberrancies occur in the fastigeal nucleus of the cerebellum there is disruption in its closed loop. These disruptions cause only one side to excite the bilateral pathway and therefore loading takes place. Loading causes an increase in facet joint approximation on one side, and causing a greater preponderance of angulation to that side. Shifting of the head (head tilt) creates the disparity of the eyes, forcing a compensation in head position to remain level with the horizon. In early development, it is these abnormalities that create changes in the symmetry of eye movement and disparities are established.

The midline nuclei of the brainstem integrate information that causes development of the erector spinea muscles. When there is a dominance of input or excitation to an individual a disparity in proper neurologic function begins. The disparity is the greater development of one hemisphere compared to the other. The learning process receives its greatest input from the visual system. When youngsters with learning differences are examined, noticeable differences are found in hemispheric dominance.

When present, dominance has been established causing the student to learn with less than 100% of their resources. Dr. Caroline Rao, et al., The Lancet (351:1849–52). This group concludes that the altered structure symmetry seen in dyslexia is a manifestation of the abnormal development of the associated neurons or their intercellular connections or both. This group, however, has been investigating brain chemistry, which requires invasive procedures. Brain chemistry results show that deficiencies continues to exist to some degree in all individuals. While there appear to be varying degrees of learning problems, but the entire population is effected in one way or another.

Much is known concerning the ability of light to affect the stability of a person's energy, mood, sleep, concentration and the regulation of a person's circadian rhythms. Light deprivation, for example, causes fatigue, irritability, anxiety, weight gain, social withdrawal and a lack of alertness. The use of light therapy has been used to treat patients that have been afflicted with several types of brain disorders. U.S. Pat. No. 5,562,719, issued to Lopez-Claros, describes one such method for treating seasonal affective, disorder, a condition affecting 5–20% of the population in areas of the country with decreased light levels throughout the year. U.S. Pat. No. 5,465,939, issued to Ochs, describes a method for assessing and amelioration of brain function after psychological and mechanical trauma. Dr. Levinson, in his world wide web site mentions successful light wave specific therapies and optometric exercises.

The human brain produces detectable signals that vary in strength and frequency over time. Human brain signals are detectable as electromagnetic waves and vary from one part of the brain to another and may, in fact, vary over time. Electromagnetic waves with different frequencies are associated with different moods and mental abilities. For example, a brain frequency of 134 Hertz or higher is know as a "beta rhythm" and is normally associated with daylight activity when all five sensory organs are functioning. In contrast, a brain wave with a frequency of 8–13 Hertz is known as a "alpha rhythm" and is associated with a relaxed creative state. Brain waves known as "theta rhythm" and "delta rhythm" have frequencies of 4–8 hertz and 0.5–4 hertz, respectively. Theta-rhythm abnormalities have been associated with learning disabilities in adolescents.

Two biochemical compounds have been implicated in the control of brain patterns and rhythms: melatonin and serotonin. Melatonin, a metabolite of serotonin, is a biochemical neurotransmitter associated with the response of the brain to light stimuli to the eye. Dr. Rao found biochemical differences between brains of dyslexic and normal men. Attempts at changing brain biochemistry by therapeutic drug regimes are greatly limited by side effects. M. J. Koepp, in an article in the May 21, 1998 issue of Nature Magazine (393: 226–268), however, states that volunteers playing a video game or staring at a blank TV screen for 50 minutes experienced a surge in dopamine similar to levels used to treat children with attention deficit disorder. After the game ended, the dopamine levels decreased, but were still higher compared with pre-game levels.

Until recently there has been no instrument to observe and record perceptual activity of the human brain. Cortical perceptual mapping (CPM) provides researchers and educators with a powerful tool to evaluate the effect of therapeutic intervention with regard to learning and the associated behavioral problems. Using CPM it has been found that physiological blind spot mapping (PBSI) of the eye provides a window to changes in cortical perceptual mapping. Increased ability to process information leads immediately to a decrease in the size of the blind spot. CPM was used extensively to development the EYELIGHTS apparatus disclosed herein as well as developing the therapeutic regimens used for the treatment of patients.

In FIG. 1, a representation of the neurological anatomy of the optical system is generally depicted as 10. Generally depicted is an eye 20 associated and controlled by the dominant cerebral hemisphere. Also depicted, is a non-dominant eye 30 associated with, and connected to, the non-dominant cerebral hemisphere. Dominant eye 20 and non-dominant eye 30 are connected via nerves 40 to the brain 50. A surface 11 is in close proximity to the dominant eye 20 and the non-dominant eye 30. The non-dominant eye 30 is stimulated by lights 12 on the surface 11 that serve to stimulate the nondominant eye 30 at a greater intensity than lights 12B that stimulate the dominant eye.

The surface 11 may be, for example, a planar or concave surface, such as sunglasses in this particular description, compared to other previously mentioned applications. The surface 11 is fitted with one or more lights 12, or using a source that can carry light such as fiber optics. In one embodiment the number of lights 12 associated with each eye is four. The number of lights may be greater depending on the needs of the patient. The lights 12 are mounted on, or integral to, the surface 11. The lights 12 may be, for example, white light, multicolored light, or plane polarized light. If the lights are multicolored, they may be primary colors or a combination of primary colors to achieve other color combinations. The lights 12 may be turned on and off by a self-contained microcontroller 41. Alternatively, the frequency and intensity of the light 13 produced by the lights 12 may be independently powered and controlled by an operator.

The lights 12 and microcontroller 41 may be an integral part of the surface 11 and may have a self-contained power source 42. The self-contained power source 42 may be, for example, a small battery or may use a solar powered source. Alternatively, the power source 12 may be electrically connected to the microcontroller 41 and the surface 11 via wires 43.

In operation, light 13 passes through the pupil 22 of the non-dominant eye 30 and stimulates the rods and cones 24 located in the retina 25 of the non-dominant eye 30. Light 13 is reflected on each of the four known quadrants of the retina 25 depending on which light 12A is activated. By projecting the light 13 on all four quadrants of the retina 25, the light 13 and the images created on those visual fields are projected onto the retina 25 upside down and in reverse. The signal produced by the rods and cones 24 activates ganglion cell axons 27 that carry visual information from the four quadrants on the retina 25. The nervous pulses traveling through the ganglion cell axons 27 converge toward the optic disk 23 in an orderly fashion, in order to maintain approximately the same relation to each other as they reach the optic disk 22. The visual signal is then passed along the optic nerve 28 onto the optic tract 31. The visual signal synapses into the lateral geniculate body 32 allowing cortical radiations 33 to travel back to the occipital lobe 34 before ascending to the cortical motor strip in the frontal lobe of the brain. The dominant eye is stimulated by lights 12B in the same manner, but to a lesser extent.

The apparatus and method of the present invention may be practiced using a variety of illumination intensities. In addition to different illumination intensities, different patterns and frequencies of lighting may be used to stimulate the four quadrants of the retina 25 in different manners, depending on the needs of the individual patient. It is found through examination that there are particular frequencies that are more suitable to different individuals. As well as the intensities of the light depending on ones ability to see and perceive the light. Those having very large physiological blind spots may require a greater intensity of light.

Figure 2:
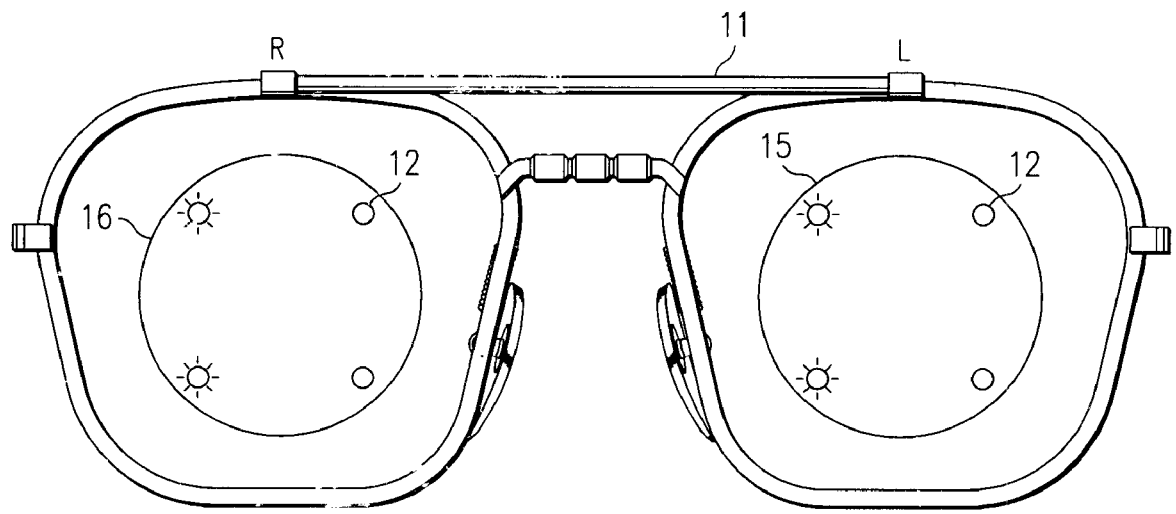
FIG. 2 is a schematic representation of the optical stimulant of the present invention.

FIG. 2 depicts a schematic representation of an apparatus for providing light 13 to the four quadrants of the retina 25 in order to stimulate the non-dominant cerebral hemisphere greater than the dominant cerebral hemisphere. Depicted in FIG. 2 is a surface 11, in this case, on the form of sunglasses that permit little or no light to pass through the lenses. While sunglasses are depicted, it will be understood by one skilled in the art that optical or transparent glasses that allow modified or normal light to pass through may be used. In an alternative embodiment, the glasses may be transparent, but the patient may be placed in a darkened room. Alternatively, the surface 11 may also be a monocle or an eye-patch that exclusively covers only the non-dominant eye 30. In yet another embodiment, surface 11 is a reflective surface that reflects light 13 from a light source that is not integral to the surface 11. In this embodiment, light 13 is bounced off the surface 11 onto the retina 25.

The surface 11 is depicted as having a right circle 15 and a left circle 16. Spaced evenly in each of the right circle 15 and the left circle 16 are lights 12. The lights 12 are disposed generally equidistant in the right and left circles 15, 16. The lights 12 are positioned to selectively stimulate each of the four quadrants of the retina 25.

Concomitant with, or exclusive of, the light source, sound may be selectively provided to the ear connected to the non-dominant cerebral hemisphere by a sound source that selectively provides sound to the ear connected to the non-dominant cerebral hemisphere. In most cases sound is provided to the ear that is contralateral or opposite the eye associated with the non-dominant cerebral hemisphere that is being stimulated. The choice of sides is determined by the physician or other qualified person fitting the patient. In most cases the dominant ear needs no additional stimulation. The non-dominant ear will be the side that is stimulated bringing the non-dominant side up to a level more equal to the dominant side. In one embodiment the sound source may be part of a headset. In yet another embodiment, the headset is connected to the surface having the one or more lights.

Another embodiment of the present invention is an apparatus for treating learning disorders by selectively stimulating the non-dominant cerebral hemisphere greater than the dominant cerebral comprising, a surface placed in close proximity to a patient's eyes, one or more lights disposed on the surface, a microcontroller for controlling the lights, the one or more lights controlled by the microcontroller, wherein only the lights in front of the non-dominant hemisphere are activated, and a power source that provides electricity to the lights and the microcontroller.

The present invention provides a method for selectively stimulating the nondominant cerebral hemisphere greater than the dominant cerebral hemisphere comprising the steps of, identifying the non-dominant hemisphere of a patient and selectively stimulating the non-dominant visual cortex of the patient greater than the dominant visual cortex using light.

In this invention a multiplicity of lights are used to stimulate the four quadrants. The quadrants include the superior and inferior nasal quadrant, and a superior and inferior temporal quadrant. In one embodiment four lights are employed with each eye. The number of lights employed, however, may be varied based on the needs of the patient.

Figure 3:
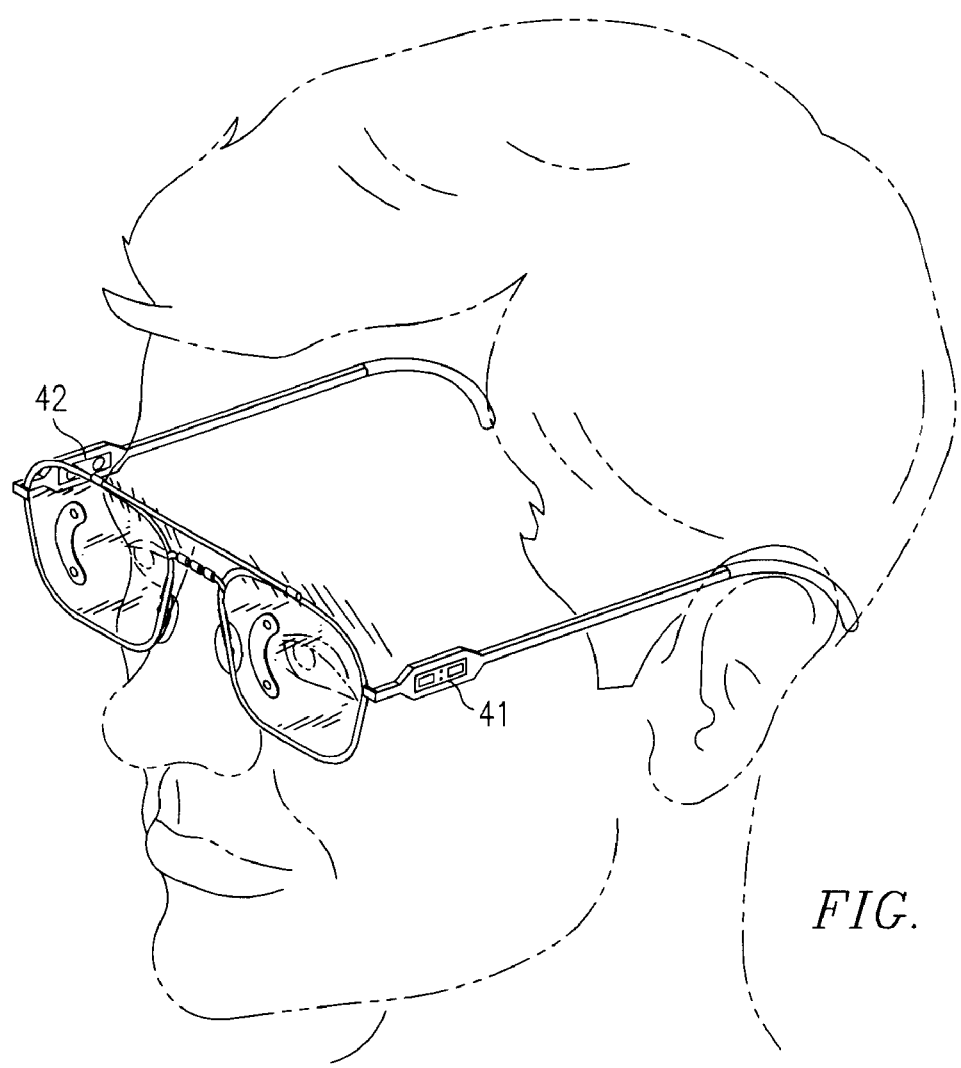
FIG. 3 is a schematic representation of the optical stimulant in a hemifield pattern.

In an alternative embodiment, illustrated in FIG. 3, hemifield stimulation is employed. In this embodiment specific quadrants are excited, e.g., two or more lights may be associated with each eye. The lights of one eye, e.g., the right eye, is focused on the temporal aspects of the patient's eye. Shining the lights on one eye stimulates the nasal or medial aspect of the eye, specifically, the superior and inferior quadrant rods and cones of the retina. Once in the retina, light excites the ganglion cells before passing through the optic nerve.

Next, light decussates through the optic chiasm to pass on to the next relay that is the lateral geniculate, before finally passing to the occipital lobe area 19 in the calcarine sulcus. The left set of lights (on the medial or nasal aspects of the patients left eye) permit stimulation of the temporal fibers, superior and inferior lateral quadrant. Stimulation follows the same pathway described above before ending in the calcarine sulcus in the occipital lobe area 19. In this pattern, the lights are focused in the inferior and superior quadrants on either the right or the left side of each eye. The neurological pathways used, will be the same as previously mentioned only that the input stimulates the side of the brain opposite the layout of the lights, i.e., lights on the right side (temporal) of the right eye and the right side (nasal) of the left eye will stimulate the left side of the brain.

An alternative embodiment of the present invention is the specific stimulation of the non-dominant auditory neurological pathway to stimulate the non-dominant cerebral hemisphere greater than the dominant cerebral hemisphere. In this embodiment differences in tone, volume and the type of auditory signal is are varied to achieve the desired effect.

In operation, a sound source, such as those found on a pair of headphones, is positioned in a patient's head and the output from the headphones is directed solely to the ear associated with, or connected to, the non-dominant cerebral hemisphere. Alternatively, the sound source may be, for example, an individual speaker that is hooked on to the ear, or is held by a strap or headset. In yet another embodiment, the sound source 44 may be attached to the surface 11. In practice both ears are actually stimulated. One ear is associated with an ear piece that would play some sort of stimulating noise. Where as the opposite ear would only be stimulated from the normal sounds of the environment. The non-dominant hemisphere is related to the ear receiving extra stimulation from an auditory device.

The volume and type of sound produced by the sound source positioned over the ear to be targeted may be controlled by the user, or by an operator via a remote connection. The type of sound may be any of a range of types of musical selections, varying from classical to jazz to the use of binomial sounds and beats. Alternatively, sounds that are not human generated may be used, such as those found in nature. Examples of sounds found in nature include, but are not limited to, ocean surf, falling rain, forest sounds and the like.

The volume and type of sound generated by the sound source over the target ear may also be varied. The sound generated by the sound source stimulates the auditory pathways to the non-dominant hemispheres of the brain. The volume may be set at a constant level throughout the treatment, or, may be varied during the treatment according to the individual patient's needs and diagnosis. As with the apparatus connected to the patient's eyes, the sound sources may be self powered, or may derive their sound and power from an independent source.

In another embodiment of the present invention, the visual and auditory stimuli to the non-dominant hemisphere may be used separately but in a serial manner. Alternatively, they may be actuated concurrently, depending on the patient's individual needs.

The present invention provides a solution to the problems of individuals that have to deal with distractions on a daily basis. These distractions take away from their optimal mental health. The present invention permits individuals with internal or external distractions to focus their mental performance and their ability to perceive information. Performance and the ability to perceive and retain information is critical to those with learning disabilities, or with a need for enhanced learning abilities. The present invention is inexpensive, thereby helping those who have financial and educational needs to afford a device that selectively increases learning potential.

The ability to focus is also critical to those in the academic, business or athletic world. Using the device of the present invention, the visual and/or auditory neurological pathways of the non-dominant cortical hemisphere of individuals can be stimulated to cause excitatory post synaptic potentials (EPSP). Selectively stimulating the non-dominant cortical hemisphere to cause collateral synaptic activity of the visual and/or neurological pathways helps to achieve the goals of optimal mental health, to focus performance and to focus the person's ability to perceive and retain information.

While the visual and auditory stimulation apparatus have been described separately, one of skill in the art will know that devices may be used concurrently. When two devices are used they may be part of a single unit, and therefore, may share the microprocessor 41 and power source 42. Alternatively, the devices may be separate and derive their power from the same source, or from independent power sources 42.

Using the light therapy system of the present invention, as shown in part in FIGS. 1–3, it was first demonstrated that the apparatus could be used to increase the learning and athletic potential or participants by changing and controlling critical brain activity of the non-dominant cerebral hemisphere in relationship to the dominant cerebral hemisphere. Next, the potential of stimulating the non-dominant cerebral hemisphere by light therapy was used to stimulate and impact the participant's mental and physical performance and well being. The apparatus and methods disclosed herein were then used not to enhance the performance of individuals in generally good health, but to treat patients with disease conditions.

The three children documented below had severe learning and behavioral problems when referred to the inventor's clinic. During consultation and subsequent therapeutic treatment of each these of young patients, the it was found that there is a distinct correlation between a strongly dominant cerebral hemisphere and learning problems. In each case, therapeutic intervention with EYELIGHTS had a dramatic effect on the students learning capabilities and disciplinary problems in the classroom.

All three children had similar backgrounds. Two came from stable environments with both parents married and living together. The third came from a divorced, yet remarried, mother and appeared to be now in a stable environment. All children were healthy and well-nourished. Another common feature was that these patients were very particular in their culinary tastes. Each was found to have a strongly dominant hemisphere.

Figures 4, 5:
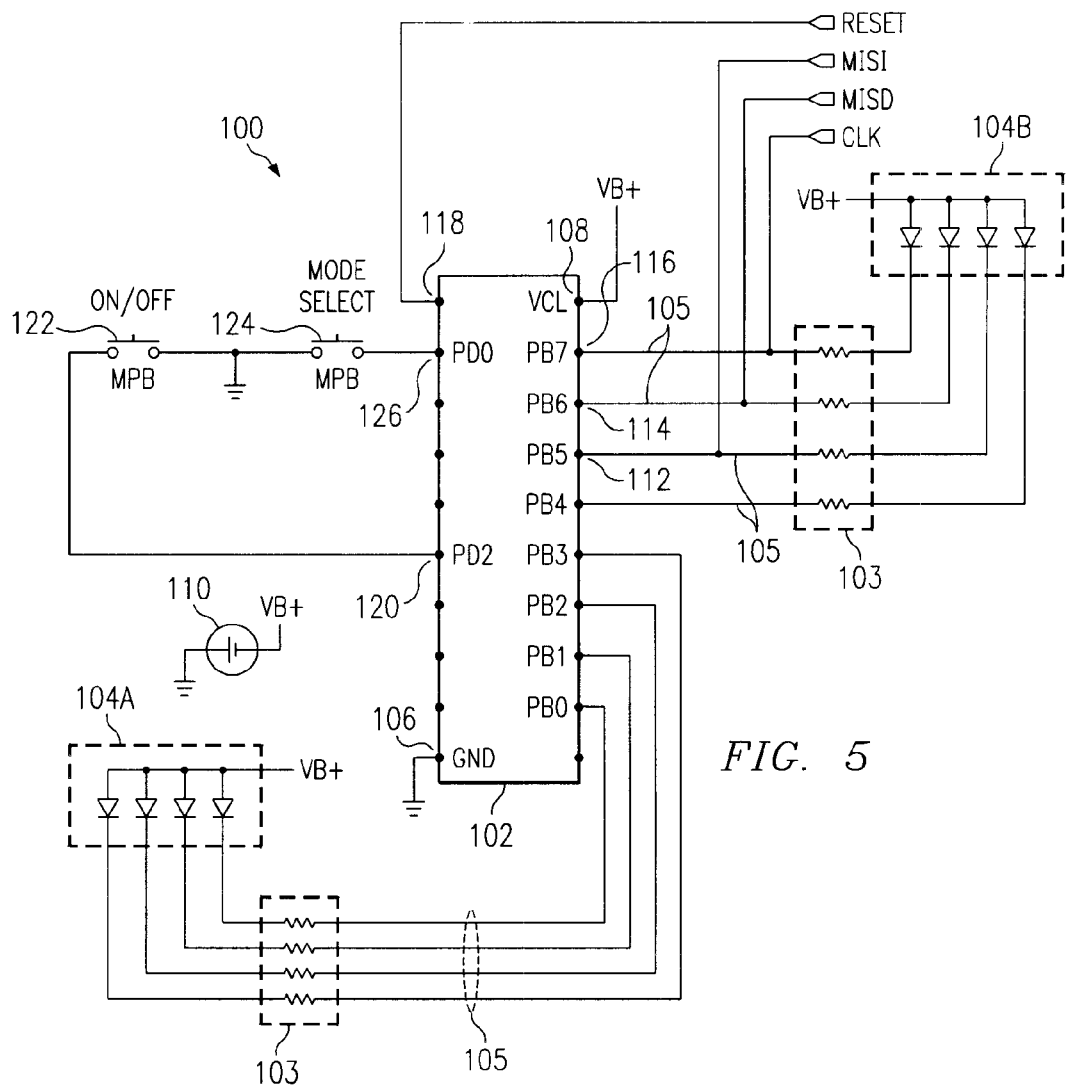
FIG. 4 is a writing sample from the patient in case study #1 before exposure to the present invention.
FIG. 5 is an 8-bit bidirectional I/O port microcontroller that provides current to the light sources.

Case #1: The patient was a boy of 6 years, 11 months. He was a very poor student after two years in kindergarten and has been socially promoted from kindergarten to the first and then to the second grade. He could not write his ABCs and had dyslexic symptoms. He was referred to therapy as the public schools had been unable to resolve his problems. The decision was made in conjunction with his parents to try light therapy using a prototype of the EYELIGHTS. Immediately prior to the installation of the glasses for the first time, the patient was asked to write his name on the chart. FIG. 4 is a writing sample from the patient prior to exposure to the present invention. The EYELIGHTS glasses were then placed on his head specifically to address his problem and he was immediately asked to write his name. FIG. 5 shows the results in writing ability after use of the present invention.

As seen above, the therapeutic regimen had a dramatic effect on the patient's pre and post ability to write his name. In FIG. 4, the student wrote his name in a mirror pattern from the right side of the paper to the left, a typical dyslexic symptom. The name shown in FIG. 5 was written immediately after the EYELIGHTS therapy was used to stimulate the non-dominant hemisphere. The student was able to write his name correctly from left to right and the letters were in the correct relationship to the baseline. The patient received three months of therapeutic treatment with one session every two weeks. His mother reports that he no longer has dyslexic symptoms, his reading and writing are improving at a rate that will bring up to his class level very soon and has no discipline problems in the classroom or at home.

Case #2: A boy of 10 years, 9 months old experienced difficulty focusing on his work and completing tests and schoolwork in a timely manner. He was consistently in trouble and behind the rest of class due to his inattention and unwillingness to partake and complete tasks at school as well as homework. During the examination, the patient was given a book from which to read in order to quickly assess his cognitive ability to learn. When asked to recite what was read he demonstrated virtually no ability to recall. Intervention with the EYELIGHTS was given and another area of the book was then read. The patient's ability to read, and his recall of the information, improved significantly. The patient also received three months of therapy with one session every two weeks.

At this time, the patient's mother and teacher report that the patient is at the top of his class and his confidence level increased along with his ability to finish and understand the task at hand.

Case #3: A boy of 6 years, 11 month old. He experienced behavioral problems, learning disorders and hyperactivity. In school he was very disruptive and was not able to sit in his chair and pay attention, or he continued to talk and upset and disturb those around him. The patient's reading was found to be from right to left and was dyslexic in his ability to write. The patient also received three months of therapy with one session every two weeks.

Post therapy changes have been significant for the patient in case study #3. The patient no longer exhibits dyslexic symptoms, presently reading and writing while staying up with the rest of his class. The patient now is able to sit in his chair and partake of classroom activity in a normal fashion.

The applications of this therapy are far-reaching. These case studies indicate that the symptoms of ADD and dyslexia may be ameliorated very quickly and at a moderate cost without chemical intervention. The therapy and the hardware may be offered through commercial learning centers, neurologists, kinesiologists, optometrists, medical doctors, psychologists and other groups with the necessary scientific training and license to perform the necessary evaluations diagnose the problem and prescribe the therapy. Government applications are also significant. For example, the therapy may be useful for enhancing military training, performance, endurance and cognitive abilities. The apparatus may also find use for the enhancement of training, resulting potentially in a reduction of training time and therefore a significant reduction in training costs.

The implementation of EYELIGHTS for this type of light therapy causes an excitation of the non-dominant hemisphere, both cerebellar and cortical and to a lesser extent to the dominant hemisphere already getting the greatest amount of the daily educational workout. The type of excitation used to implement the therapy uses a feed-forward or efferent-copy mechanism. The process complements the already dominant hemisphere with an elevation of the non-dominant hemisphere, thereby elevating the entire neuraxis.

The results obtained using the present invention may be documented scientifically as follows. A Visual Evoked Potential (VEP) measurement allows an observer to measure the speed at which the brain reacts to an external light stimulus. A VEP is comprised of three parts. Surface recording electrodes are strategically along the midline of cranium at frontal center (Fz), parietal central (Pz), and occipital central (Oz) locations. A stimulus in the form of a red and black checker board flash pattern is applied. The interaction between the perception and tile realization of light to the neuraxis is measured. The test will measure hemifield stimulation to the right and the left eyes and the test will be performed with and without the EYELIGHTS in place.

A trained observer, e.g., the patient's teacher or counselor, documents the patient's behavioral and learning tendencies at the beginning of the evaluation and therapy period. The observer establishes a baseline condition for each student both with and without the EYELIGHTS. A three-month daily therapy routine for each student will be initiated. The observer documents changes in observed behavioral and learning tendencies at intervals, e.g., weekly, during the therapy period. At the end of the therapy the observer performs an identical set of PBSI and VEP tests with and without the EYELIGHTS to establish changes from the original tests. The PBSI and VEP data and teacher observations will be correlated.

Further studies may be conducted as follows. Twenty or more students are selected from the surrounding community school systems. The students include children in elementary school, grades 1–6. To be selected the student must have been clinically diagnosed to have ADD, ADHD, or dyslexia by a child or school psychologist and the student's counselors. The parent or guardian of each child will be required to sign a consent form before entering the program. The children are split equally into a test group and a control group. It is hoped that an equal number of boys and girls may be included in the groups.

The observer will meet with the trained child or school psychologist to generate a standard observation protocol. The protocol is used during the evaluation and study periods to establish baselines and document progress and final state conditions for each student. Each student receives a thorough neurological and orthopedic examination and the results recorded. Any student with a previous history of epilepsy, migraine or seizures will be excluded from this test program.

The protocol may include, e.g., a PBSI (physiological blind spot indicators) test to determine right and left hemispheric deficiencies. Also, a baseline VEP test is performed on each student. These techniques will establish the baseline electrical activity of the brain. Three electrodes are placed along the midline of the cranium or sagittal suture. The electrodes are placed at the following locations Fz (frontal lobe center) Pz (parietal lobe center), and Oz (occipital lobe center). The measurements are gather for the interaction between the perception and the realization of light to the individual students neuraxis. Five separate brain stimulations may be performed; bilateral stimulation, right hemifield stimulation, left hemifield stimulation, right monocular stimulation, and left monoccular stimulation. This information is recorded and used to support the use of light stimulation in an individual defined with a specific cortical lesion.

Next, each student is fitted with a pair of EYELIGHTS with the correct monoccular stimulation per the results of the testing in 4) and baseline data with tile glasses will be taken as disclosed hereinabove. Following the determination of basal brain activity, the therapy period begins. Each of the students in the therapy group, under the supervision of his teacher or counselor, will be asked to wear the EYELIGHTS for a period of 5 minutes at the beginning of each school day, after lunch, and at the end of the school day. The test period may be, e.g., three months. The teacher or counselor is asked to record that the student actually completed each step in the therapy.

At the end of the therapy period each student in the therapy group and the control group will be tested as disclosed hereinabove using the protocol determined or used for that patient. During the therapy period, the teachers and counselors involved with both the therapy and control groups will be asked to document the classroom performance of each child in the study oil a weekly basis. At the end of the testing period, the test results and the observation reports are tabulated and analyzed. The correlation between the PBSI and VEP test for each patient are then established.

The following is a list of equipment that may be used to obtain the PBSI, VEP and other measurements disclosed in the protocol hereinabove, and include:

1) a Cadwell Sierra 11 Visual Evoked Potential;
2) a Physiological Blind Spot Mapper;
3) a Micromedical Technologies Real Eyes infrared frail camera and goggles;
4) a video recorder/television
5) a 8 mm video camera/VCR.

Based on the observations made with the patients in the three case studies a physiologic mechanism is proposed for the observations made using the present invention. In no way should the proposed physiologic mechanism be used to limit the scope of the present invention. It has been observed that the pontine epinergic cells are important for human survivability in regards to limbic reality because it provides epinergic neurotransmitters that drive the dopaminergic A10 cells and the superior and inferior colliculus; resulting in stimulation of the lateral and medial geniculate bodies.

These thalamic nuclei fire projections to primary association areas in the temporal lobe, parietal lobe, and area 17 of the occipital lobe.

This portion of the limbic system is important for human survival because it is responsible for firing the rostral reticular activation system of the mesencephalon that activate the cortex. Pontine epinergic cells allows the tectum to reach summation quickly, thereby informing our cortex about impending danger from the modalities light and sound (i.e., via the superior/inferior colliculus) but also it provides epinephrine for the receptors of the right limbic expression.

The right brain has a higher density of epinergic receptors than does the left brain, which is higher in dopaminergic receptors. Without proper activation of the epinergic centers a patient may experience a loss of primary humanistic drives (i.e., to eat, get up and go to work, have sex, etc.).

The amygdala is also rich in dopamine and epinephrine. In order to ascertain which system is responsible for decreased activation of the amygdala, it is necessary to compare whether the amygdalal response is associated with the dopaminergic (mesencephalic) or epinergic (pontomedullary) system. To make the distinction, it is necessary to examine the cranial nerves associated with the specific regions of the brainstem. It has been found using the apparatus and the method of the present invention, that if a patient has a decrease in epinergic activity resulting in an amygdala response or decreased pontine firing, the patient could suffer form a pontine/cerebullar type of dysfunction.

Therefore, using the present invention, it has been found that if one decreases the firing of the cerebellum, there is a high probability that there is a decrease in the activity of the pons and of the integration into the Locus cerulcus and the sub ceruicus. Decreases in mesencephalic activities of, e.g., Ed-Wes, substantia nigra, red nucleus, CN's 3,4 etc. would be indicative of dopaminergic dysfunctions. One way to increase A10 firing is to increase the FOF of neurons in the vicinity. That is the trochlear nucleus in the caudal mesencephalon. To do so one requests that the patient move their eyes down and in, towards the side of the lesion.

Epinergic systems also descend caudally and evoke stimulation to the dorsal and medial raphe nuclei and the pontomedullary junction directly increasing their FOF without going to the brain. These systems serve to attenuate secondary stimuli and allow primary stimuli (food, sex, etc.) to be pleasurable. The descending portion of the epinergic system is serotonergic and descends within the pontomedullary inhibitory projects within the ventral lateral funiculus of the cord ipsilaterally. This is the same projection that: 1) actively inhibits inhibition to the ipsilateral alpha and gamma motor pools; 2) actively inhibits the IML; and 3) actively inhibits the ipsilateral anterior compartment muscles about T6 and post compartment below T6.

When a patient loses the ability to activate this system, there is a probability that secondary stimuli may reach cortical representation. The symptomatology may present as day dreaming, states of confusion, and in some cases even suicide. It is well known that a percentage suicide victims have been shown on autopsy to have decreased levels of 5-hydroxytryptophan (5-HT, a serotonin derivative) that would be produce as a consequence of epinergic firing of the Raphae nuclei of the brainstem. When epinergic firing of the Raphae nuclei is decreased, the attenuation of stimuli also decreases and the cortex is subject to an increase in somatotopic srepresentation that exceeds metabolic rate. Hence, potential suicide. Using the cerebellar stimulation method and apparatus of the present invention control over (feedforward, feedback, and efferent copy) cranial nerve stimulations is shown herein to help control limbic dysfunction's.

As already mentioned, the amygdala is an area that is very important to human survival. Children have limited integration into the amygdala from the frontal lobe due to a lack of cortical plasticity. It is a loss or lack of the inhibitory mechanism from the frontal lobe that causes kids to "say and do the strangest things" that most adults would not. A child builds plasticity within the integrating pathways to the amygdala either from physical stimuli through cerebellar feedback pathways or the comforting feedforward pathways from a mother's love. The integration and expression of the amygdala into the limbic system depends on so many factors that doctors in general, only make predictions of how and why things developed the way they did.

Reference is now made to FIG. 5, in which a schematic diagram of a system 100 is shown in accordance with one embodiment of the present invention. System 100 includes a microcontroller 102 that controls various functions of the circuit 100, including sending and receiving electrical signals. Microcontroller 102 includes programmable flash memory for, e.g., storing code. Microcontroller 102 may typically be a conventional device such as, for example, a AT90S1200 microcontroller manufactured by Atmel, or other such commercially available devices.

Microcontroller 102 sends electrical signals through resistors 103 to light sources 104A and light sources 104B (collectively, light sources 104) via electrical interfaces 105. Light sources 104 may be conventional light emitting diodes (LEDs). In the embodiment depicted in FIG. 5, in which the number of light sources 104 is eight, four light sources 104A may be associated with a patient's first eye, and four light sources 104B may be associated with a patient's second eye; however, as mentioned previously, it should be appreciated by one skilled in the art that the number of light sources 104 may be varied according to the requirements, diagnosis and preferences of the patient.

In the embodiment shown in FIG. 5, port B of microcontroller 102 is an 8-bit bidirectional I/O port that provides current to light sources 104. When pins of port B are used as inputs and are externally pulled low, they will source current if the internal pull-up resistors are activated. It should be understood by one skilled in the art, however, that an active high device may be employed consistent with operation of the present invention.

Port pin 106 of microcontroller 102 functions as a ground pin (GND). Port pin 108 of microcontroller 102 functions as a supply voltage pin (VCC). FIG. 5 depicts a battery 110, which may be approximately 3 volts, as a suitable supply voltage. It should be appreciated by one skilled in the art that the present invention is not limited to the described supply voltage but is intended to encompass a broad range of supply voltages according to the specifications of microcontroller 102.

Port pin PB5 112 of microcontroller 102 has an alternate function as a data input line for memory downloading (MISI). Port pin PB6 114 of microcontroller 102 has an alternate function as a data output line for memory uploading (MISO). Port pin PB7 116 of microcontroller 102 has an alternate function as a serial clock input (CLK).

A low level on Reset pin 118 of microcontroller 102 for a certain time period, for example, longer than approximately 50 ns, will generate an external reset. An external interrupt may be triggered by setting port pin PD2 (INTO) 120 of microcontroller 102. As shown in FIG. 5, an on/off switch 122 is connected to port pin PD2 120. A switch 124 is connected to port pin PD0 126 of microcontroller 102, and functions as a mode selector, rotating among the available modes.

The intensity of each of light sources 104 may be increased or decreased as desired by making adjustments in duty cycle. For example, microcontroller 102 may pulse one of light sources 104 such that it is on for 10 ms, and then off for 30 ms. To achieve a higher intensity, microcontroller 102 may pulse one of light sources 104 such that it is on for 30 ms, and off for 10 ms.

Figure 6:
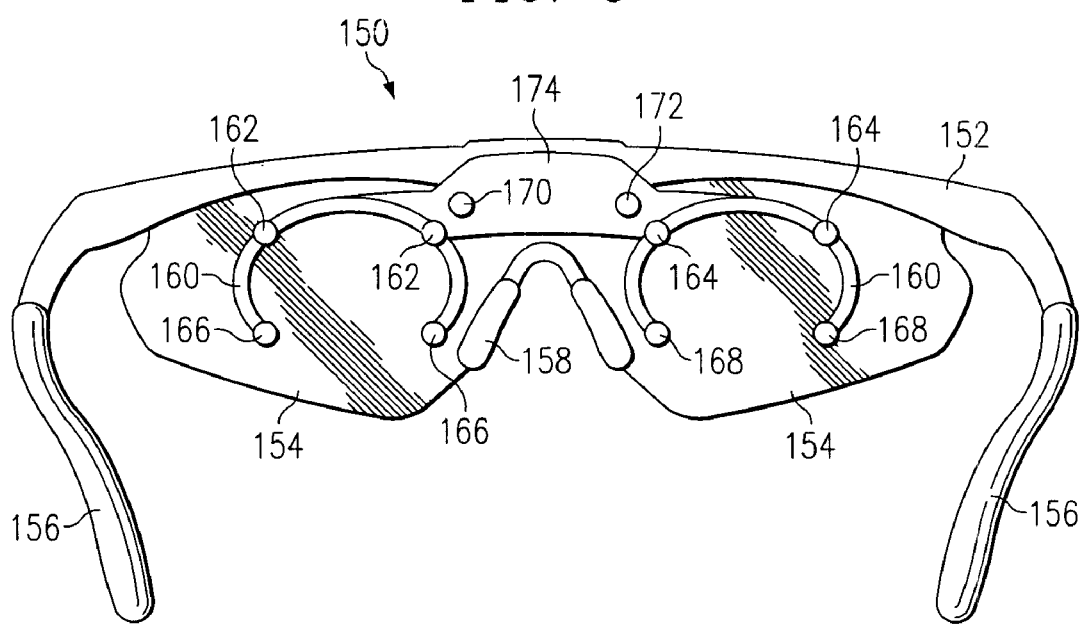
FIG. 6 depicts a rear elevation view of a device employing the features of current system.

FIG. 6 depicts a rear elevation view of a device 150 employing the features of system 100. Device 150 includes a first frame 152, lenses 154 mounted therein, temples 156 connected to the first frame 152 via hinges (not shown) and a nose piece 158. Attached to the first frame 152 is a second frame 160, on which two upper left LEDs 162, two upper right LEDs 164, two lower left LEDs 166 and two lower right LEDs 168 are mounted. Further included in device 150 are a power switch button 170, a mode selector switch button 172 and a battery receptacle 174. The second frame 160 may be removably attached to the first frame 152 via snaps, for example.

To stimulate the temporal area of a patient's brain, where learning and memory functions are located, if the patient's right eye is dominant, the power switch button is depressed until a set of LEDs are illuminated. The mode selector switch button 172 is then depressed until the upper left LEDs 162 are flashing brighter than the lower left LEDs 166. In order to stimulate the temporal area of a patient's brain, e.g., where the patient's left eye is dominant, the power switch button is depressed until a set of LEDs are illuminated, and the mode selector switch button 172 is then depressed until the upper right LEDs 164 are flashing brighter than the lower right LEDs 168.

To stimulate the parietal area of the patient's brain, where sensory and motor functions are located, if the patient's right eye is dominant, the power switch button is depressed until a set of LEDs are illuminated, and the mode selector switch button 172 is then depressed until the lower left LEDs 166 are flashing brighter than the upper left LEDs 162. In order to stimulate the parietal area of a patient's brain, e.g., where the patient's left eye is dominant, the power switch button is depressed until a set of LEDs are illuminated, and the mode selector switch button 172 is then depressed until the lower right LEDs 168 are flashing brighter than the upper right LEDs 164.

Figure 7:
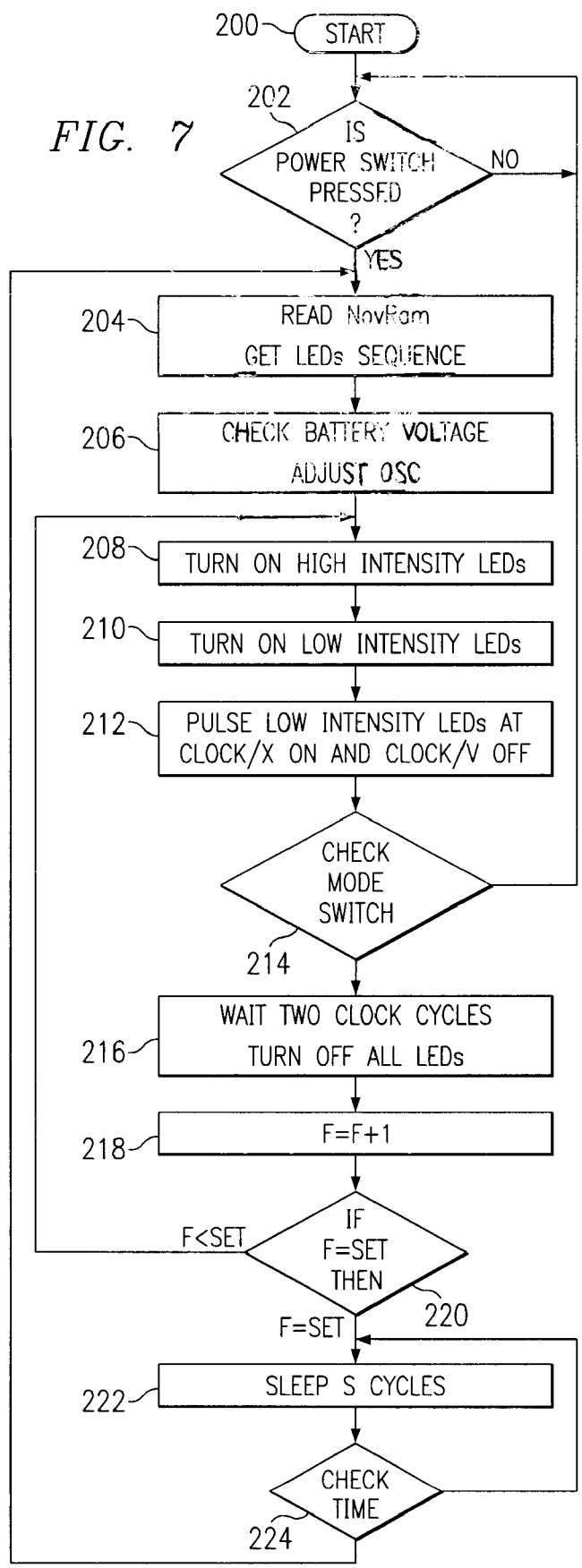
FIG. 7 is a flow diagram of the process steps that may be executed by the code embedded in microcontroller in accordance with one embodiment of the present invention.

Reference is now made to FIG. 7, which depicts a flow diagram of the process steps that may be executed by the code embedded in microcontroller 102 in accordance with one embodiment of the present invention. Process flow starts at step 200, and a power check is initiated in step 202. If the power is on, process continues to step 204, in which the Non Volatile RAM is checked to see if a particular mode was set during a previous run. If there is no previous set state, the system is powering on for the first time. If the system 100 was powered on previously, a mode will be stored in the Non Volatile RAM and automatically read into data registers.

Next, in step 206, the voltage of VCC at port pin 108 is read, and the internal oscillator of microcontroller 102 may be adjusted accordingly. In steps 208 and 210, the appropriate light sources are turned on. The light sources are then pulsed in step 212 such that they are on for a certain length of time and off for a certain length of time pursuant to a prescribed duty cycle.

The mode switch is checked in step 214, and if the mode switch is set to a particular value, then process flow continues to step 216. After an appropriate amount of clock cycles, all light sources are turned off. Otherwise, the process flow reverts to step 204.

In step 218, a counter is incremented and then compared to a predetermined value in step 220. If the counter is less than that value, then process flow loops to step 208; if the counter is equal to the predetermined value, then process continues to step 222. Microcontroller 102 then sleeps for an appropriate number of cycles in step 222, and time is checked in step 224 to determine whether the microcontroller 102 should continue sleeping, or whether process loops back to step 204. Code for implementing this process is shown in Appendix I.

---

APPENDIX I

```
;   TC0 runs with prescale=1. no reloading necessary.
;       interrupt frequency is approx 4KHz. LEDs are
;       brightness controlled by being on for (between 1
;       and 16) out of every 16 ticks, reducing frequency
;       to approx 250 Hz.
;
;   Brightness control works as follows:
;       At the BEGINNING of a brightness control cycle, if
;       the Flash Duty Cycle counter says that the LEDs
;       should be ON, then both the High and Low Intensity
;       LEDs are turned on.
;       After the appropriate amount of time, the Low
;       Intensity LEDs are turned off to perform Brightness
;       control. Later, the High Intensity LEDs are turned
;       off. Even later, the Duty Cycle count point is
;       reached, and the Brightness Control Cycle begins
;       again.
;   LEDs are driven thru separate resistors: LOW=ON.
;       All LEDs are on Port B to simplify software.
;
;   Button Functions:
;       One button serves as the power control. It is tied
;       to PD2, so it can wake up the AVR from full power-
;       down mode by using a low-level int. The other
;       button rotates between the available modes.
;   Button denounce method:
;       When pressed, action occurs immediately. Debounce
;       action comes into play by waiting a defined time
;       before re-checking the switch to see if it has been
;       released yet or not.
;   Watchdog:
;       The watchdog is used to wake up the processor to
;       check for button presses. It is also used to do
;       the 20-second OFF time while running.
;
;   RESET-based startup conditions:
;       OFF20:      dec ctr. If =0, go to ON20 mainline
;                   handler to restart 20-sec flashing. If
;                   not =0, check for on/off button. If
;                   seen, do powerdown lights & debounce
;                   button, then go into Wdog sleep
;                   condition. If button not pressed, go
;                   into Wdog Sleep.
;       POWERUP:    init variables, go into IDLE mode. Don't
;                   check buttons. Also, kick all lights on
;                   Full Intensity
;       IDLE:       check for On/Off; if seen, recall stored
;                   EE LED mode, force onto lamps while
;                   On/Off button remains pressed. After
;                   release & debounce, go into ON20 mode.
;       ON20:       If this condition should occur, do IDLE.
;   INTERRUPT-based conditions:
;       ON20:       timer tick runs first, then RETIs into
;                   mainline. Mainline checks for On/Off &
;                   Mode button; if none, goes back into
;                   Idle-sleep.
;       IDLE:       in this condition, just output the
;                   current LED state as defined in HiLights
;                   & LoLights, without doing any 7.77Hz
;                   flashing. This is used at power-down as
;                   well as mode-change and powerup.
.include "1200def.inc"
.equ MAINCLOCK =    170000   ;CPU clock (either internal or
                                ext.)
.equ FLASHRATE =    777      ;LED main blink frequency,
                                TIMES .100
.equ WATCHDOG =     MAINCLOCK ; (internal RC osc on AVR chip)
```

-continued

APPENDIX I

```
.equ WDOGRATE =     (WATCHDOG / 1024) / 128    ;
                    (frequency)
.equ OnSeconds =    4         ;# of secs that LEDs blink
                              while running
.equ Offseconds =   7         ;# of secs they're BLANK while
                              running
;This number is the total number of timer ticks in one
brightness control period.
.equ DutyBright =   16
;This setting is the number of ON-ticks for a HIGH-brightness
LED
.equ HighBright =   16   ;(allowable range is from 1 to
                              DutyBright)
;This setting is the number of ON-ticks for a LOW-brightness
LED
.equ LowBright =    3    ;(1 is the minimum allowable
                              setting)
.equ ModesInUse =   8    ;set this to 6 if using modes 0–5,
                              or etc.
;Customize for each desired pattern. Any LED not included
will be OFF.
.equ Pattern0H = 0x90    ;adjust these to fit mode selection
.equ Pattern0L = 0x60
.equ Pattern1H = 0x60
.equ Pattern1L = 0x90
.equ Pattern2H = 0x09
.equ Pattern2L = 0x06
.equ Pattern3H = 0x06
.equ Pattern3L = 0x09
.equ Pattern4H = 0x81
.equ Pattern4L = 0x42
.equ Pattern5H = 0x42
.equ Pattern5L = 0x81
.equ Pattern6H = 0x18
.equ Pattern6L = 0x24
.equ Pattern7H = 0x24
.equ Pattern7L = 0x18
;--------------------------------------------------------
.def SaveSreg =     r0       ;holder for SREG during ISRs
.def Alive0 =       r1       ;is it running presently?
.def Alive1 =       r2
.def Alive2 =       r3
;3912Hz rate src (1MHz. /256)
.def BrightCtr =    r16      ;counts sets of 16, is COMPARED
                              AGAINST.
.def FlashCtr =     r17      ;to time the 7.77mS flash rate
                              & duty cycle
.equ DutyFlash =
             (((MAINCLOCK/256)*100)/DutyBright)/FLASHRATE)
.equ OnFlash =      (Duty Flash / 2)    ; if DutyFlash
                                         is odd, make ON
                                         short
.equ OffFlash =     DutyFlash - OnFlash  ; allow OFF to
                                         be the longer
                                         one
;DutyFlash =        125 if CLK=4MHz       ; =31 if CLK=1MHz;
                                          =11 if CLK=350KHz
.def Ctr20 =        r18      ;used for timing the 20-
                              sec interval
.equ On20sec =      OnSeconds*FLASHRATE/100    ;how many
                    (7.77Hz) flashes to do
.equ Off20sec =     OffSeconds*WDOGRATE    ;how many Wdogs
                                            occur during OFF
.equ WDOGSETTING =  0X0B   ; = approx. 0.125sec (is the /128
                              setting)
.def OpMode =       r19
.equ POWERUP =      0x00   ; (RAM is cleared at initial power-
                              on)
.equ IDLE =         0X01   ;in an inactive mode
.equ OFF20 =        0x02   ;timing the 20-sec OFF period
.equ ON20 =         0x03   ;doing the 20-sec ON period
.def KeyState =     r20    ;which key being pressed
.def KeyCount =     r21    ; how many sets of 10mS for debounce
.def TickCtr =      r22    ;inc this every tick; misc usage.
.def LEDMODE =      r23    ; hold LED pattern selection (a copy
                              of EE)
```

-continued

APPENDIX I

```
.def HiLights =     r24    ; hold bit positions of current Hi-
                              Intens LEDs
.def LoLights =     r25    ; hold bit positions of current Lo-
                              Intens LEDs
.def ISR0 =         r28    ; reserved for use by ISR only
.def temp2 =        r29
.def temp1 =        r30    ;used by mainline
.def temp0 =        r31
.def ZL =           r30
.def ZH =           r31
.equ ButtonPin =    PIND
.equ ONOFFSW =      2
.equ MODESW =       0
.equ MaxModes =     4      ;this defines max possible # of
                              modes
;==================================================
.org 0
RstVec: rjmp  Startup
TR00:  rimp  OnOffButton  ;PD2, Ext. Int. 0
                          (wakeup)
;the following NOPs are placeholders for INT vectors on 8515,
so the code will run on both the 90S1200 & the 90S8515 w/ no
changes.
       rimp  Timer0        ;INT1
       nop                 ;T1capt
       nop                 ;T1compA
       nop                 ;T1compB
       nop                 ;T1ovf
Timer0: ;this is the (approx) 4KHz timer tick
       in    P0.SREG
       inc   TickCtr       ;misc usage
       inc   BrightCtr     ;bump Brightness duty cycle
                              counter
       cpi   BrightCtr.DutyBright  ;at end of Bright
                                    Control Cycle?
       brne  DoBrightness  ;if not, check for Low/Hi steps
       clr   BrightCtr     ;reset the brightness control
                              counter
;Completed one full cycle of brightness duty-cycling now.
       cpi   OpMode.IDLE   ;if IDLE mode, don't turn off
                              LEDs!
       breg  LightsOn
;not IDLE mode, so go ahead and FLASH the lights.
       inc   FlashCtr;bump the Flash Rate timer
       cpi   FlashCtr.DutyFlash  ;at end of Duty Cycle
                                  period?
       brne  ChkOffFlash   ;if not, see if in OFF
                              time of 7.77Hz
       clr   FlashCtr
;Done  with one 7.77Hz period now.
;Turn ON LEDs f not at end of 20-sec ON-period.
       inc   Ctr20
       cpi   Ctr2O,On2Osec
       brne  LightsOn; 20-sec ON time still going!
;need to drop into 20-sec OFF time now
       ldi   Ctr20.Off20sec   ;set up Wdog tick count
       ldi   OpMode,OFF20     ;set new mode!
WDSLEEP:
       cli                   ;kick the dog!
       wdr
       ldi   ISR0,WDOGSETTING
       out   WDTCR,TSR0
;      ldi   ISR0.0x00       ;shut off ext int
;      out   GIMSK.ISR0
       ldi   ISR0.0x30       ;PowerDown mode. w/ low-level
       out   MCUCR.ISR0      ;external interrupt mode.
;      ldi   ISR0.0x40       ;Enable ext int!
;      out   GIMSK,ISR0
;      sei                   ;Enable all ints
       sleep                 ;we'll get a Reset from
             WDT
;      nop
       rjmp Startup ;this is here JUST IN CASE ...
ChkOffFlash:
       cpi   FlashCtr,OffFlash   ;if at or above this
                                  count.
       brsh  HighOff;            ;don't turn the lights
```

APPENDIX I -continued

```
                            on!
LightsOn: ;turn on LEDs according to current Mode
            mov     ISR0.HiLights   ;grab bits for Hi-Intensity
            or      ISR0,LoLights   ;merge bits for Lo-Intensity
            com     ISR0
OUTLED:     out     PORTB.TSR0
RTI: ;go to Main to check Mode button, then go into Idle mode.
            in      R0,SREG
            reti
.DoBrightness: ;check for when to turn OFF the LED banks
            cpi     BrightCtr,LowBright  ;shut off some yet?
            breg    LowOff
            cpi     BrightCtr,HighBright
            brne    RTI
Highoff: ;turn off Hi-Intensity lights now
            ldi     ISR0.0xFF       ;just turn ALL LEDs off
            rjmp    OUTLED
PwrTbl: ;constant sequence for power management
            .dw     0x3572,0x2165,0x4F43,0x5950
            .dw     0x4952,0x4847,0x2054,0x3931
            .dw     0x3939,0x5220,0x4720,0x4620
            .dw     0x4952,0x5345,0x4423,0X3700
LowOff: ; turn off Low-Intensity lamps now
            in      ISR0.PORTB      ;read LED status
            or      ISR0.LoLights   ;force ONLY the Lo's HIGH (off)
            rjmp    OUTLED
;====================================================
Startup:                ;check if were alive before got reset
            ldi     temp0, 0x80    ,turn off comparator
            out     ACSR,temp0     ; to save power
            ldi     temp0,0xFF     ;set up stack for 8515
                                   (test only)
            out     0x3D.temp0
            ldi     temp0.0x01
            out     0x3E,temp0
            ldi     r29,0x52 ;set up a unique string
            ldi     r30,0x47 ; that would NOT be present
            ldi     r31,0x46 ; at initial powerup...
            cp      r29,Alive0     ;Is the string present in RAM?
            cpc     r30,Alive1
            cpc     r31.Alive2
            breq    Resume         ;Jump if string already there!
    ;At this point, we've not been awake before. Init the
    chip, see if a button is pressed and handle it, or go
    into SLEEP mode with On/Off button interrupt armed.
ClearM:     ldi     ZH,0            ;clear memory before proceeding
            ldi     Zl,30
ClrMem:     dec     ZL
            st      Z.ZH
            brne    ClrMem          ;if Z > 0, loop
            ldi     temp0.0x52      ;init unique-string
            mov     Alive0,temp0
            ldi     temp0.0x47
            mov     Alive1.temp0
            ldi     temp0,0x46
            mov     Alive2,temp0
Resume:     :after *Reset, must ALWAYS re-init ports &
peripherals
            ldi     temp0.0xFF              :init the LED port
            out     PORTB.temp0             :force all LEDs off
            out     DDRB,temp0              ;set dir to OUTPUT
            out     PORTD,temp0             ;turn on ALL pullups on PORTD
;--------------------------------------------------------
-------
OK:
;Now determine currrent RESET mode & react accordingly.
    ;check if timing the 20-sec OFF period
            cpi     OpMode.OFF20
            brne    ChkModel
    ;we ARE in OFF20 mode.
            dec     Ct420
            breg    DoneOFF20       ;just finished OFF time, so go
                                    wake up!
    ;Still in the 20-sec OFF period, but check for ON/OFF
    button!
            sbjc    ButtonPin.ONOFFSW
            rjmp    WDSLEEP         ;go to sleep again
    ;ON/OFF button is pressed, so kick on all lights until
    released.
    ; and then go into WDOG SLEEP mode (or NO-WDOG SLEEP if
    use PD2).
PwrOff:     ldi     TickCtr, (256-40)    ;approx 10mS debounce
PwrOff1:
            ldi     OpMode.IDLE
            clr     LoLights; force all LEDs to high intensity
            ser     HiLights
            rcall           StartTimer
            sei                             ;global enable ints
PwrOffLoop:
            cpi     TickCtr.0
            brne    PwrOffLoop              ;wait here for 40 ticks
PwrOffLoop2:
            sbis    ButtonPin.ONOFFSW    ;stop looping if released
            rimp    PwrOffLoop2
            cli
            ldi     temp0.0xFF              ;turn off LEDs
            out     PORTB.temp0
            rjmp    WDSLEEP         ;enter SLEEP, in IDLE state, no
    button!
DoneOFF20:      ;have lust finished timing the 20-sec OFF
period.
    ;start up the Timer again now
            rcall   StartTimer
;   ;set up the On/Off button interrupt
            ldi     temp0.0x00              ;shut off ext int
            out     GIMSK.temp0
            ldi     temp0.0x22              ;SLEEP='IDLE'   .   w/
                                            falling-EDGE
            out     MCUCR.temp0 ; interrupt sense
            ldi     temp0.0x40              ;enable ext int
            out     GIMSK.temp0
    ;set new operating Mode
            ldi     OnMode,ON20  ;assert new mode status
    ;watch the Mode & On/off buttons from now on...
            rjmp            CheckButton
;----------------------------------------------------------
---
ChkModel:   ;next, check if we lust had initial power-up
            cpi     OnMode.POWERUP ;did we just power up?
            brne    ChkMode2
    ;force into IDLE State, but kick on lamps BRIEFLY first
            ldi     TickCtr,1       ;approx 62mS
            rjmp    PwrOff1
;----------------------------------------------------------
---
ChkMode2:   :if IDLE, waiting for ON/OFF button press to
activate!
            cpi     OpMode,IDLE
            brne    ClearM                  :got a completely
    unknown reset
    ;woke up to check for ON/OFF button press
            sbic    ButtonPin.ONOFFSW
            rimp    WDSLEEP         ;no button, so go back to sleep!
    ;ON button pressed, so restart previous mode
            rcall           GetLEDmode
            rcall           SetUpLEDs
            ldi     Ctr20.0
            ldi     OpMode.ON20
            rcall           StartTimer
            ldi     KeyState.1      ;set up to debounce PowerOn
condition
            ldi     KeyCount.60
    ;now go into light-sleep mode, then loop waiting
    for either
    ;a mode change or a power-off request. Whenever we
    power off, we must save new MODE value to EEPROM if
    it changed during operation. This can be
    determined by checking current mode against what's
    in EE, and if different, store the current.
CheckButton:    ;this monitors the Mode button after a Timer
Tick
            ldi     temp0.0x22      ;Idle Mode, failing-EDGE ext int
            out     MCUCR.temp0
            sei                             ;enable ints again
```

APPENDIX I (continued)

```
            sleep
            nop
       ;check button denounce first
            cpi    KeyCount,0      ;are we debouncing?
            breg   CBonoff
       ;we ARE debouncing, but which one?
            cpi    Keystate,1      ;is it power-on?
            brne   DBMode
       ;we are debouncing the On/Off button
            sbis   ButtonPin,ONOFFSW
            ldi    KeyCount,60     ;restart 15ms timer
            dec    KeyCount
            rjmp   CheckButton     ;always loop back now.
DBMode:                            ;debouncing the MODE button
            sbis   ButtonPin.MODESW
            ldi    KeyCount,60     ;restart 15ms timer
            dec    KeyCount
            rjmp   CheckButton     ;always loop back now.
Cbonoff: ;check On/Off button first!
            sbic   ButtonPin,ONOFFSW
            rimp   CBMode
       ;handle power-down now
            rcall         SaveMode ;save LEDMODE if needed
            rjmp   PwrOff          ;wait for button release too
       CBMode: ;check the MODE button now
            sbic   ButtonPin.MODESW
            rimp   CheckButton     ;loop back if not pressed
       ;button is pressed.
            clr    KeyState
            ldi    KeyCount,60     ;15mS
            inc    LEDMODE         ;bump and
            andi   LEDMODE.7
            cpi    LEDMODE,ModesInUse ;check against max used
            brlo   CBModel
            clr    LEDMODE
CBModel:
            rcall  SetupLEDs
            clr    Ctr20
            rjmp   CheckButton     ;loop back
;This can be called from one of three means;
;    1) during 20-sec ON-time of LEDs, via EDGE interrupt
;    2) during 20-sec OFF-time, via LOW-LEVEL int
;    3) during UNIT-OFF, via LOW-LEVEL int
;    Debounce is handled differently for EDGE-mode vs LEVEL.
;    For LEVEL debounce, we switch to IDLE mode until get a
;    high-edge indicating (button release), then if no more
;    edges are seen for 50mS, assume the button is debounced.
;    If an EDGE-based request comes in, it MUST be to power
;    off the device, so shift off LEDs, wait for button
;    release, then wait 50mS; if not pressed then, power down.
OnOffButton:      ;external interrupt service routine
;-------------------Utilities-------------------
--
GetLEDmode:
            ldi    temp0.0x01      ;address where we keep Mode
       #
            out    EEAR,temp0
            out    EECR,temp0
            out    EECR,temp0
            clr    temp0
            out    EEAR.temp0      ;wipe out address in case
of flaw
            in     LEDMODE,EEDR
            ret
SetUpLEDs:
            andi   LEDMODE,MAXMODES-1 ;mask first!
            cpi    LEDMODE,0
            brne   SUL1
            ldi    HiLights,Pattern0H
            ldi    LoLights,Pattern0L
            ret
SUL1:       cpi    LEDMODE,1
            brne   SUL2
            ldi    HiLights,Pattern1H
            ldi    LoLights,Pattern1L
            ret
SUL2:       cpi    LEDMODE,2
            brne   SUL3
            ldi    HiLights,Pattern2H
            ldi    LoLights,Pattern2L
            ret
SUL3:       cpi    LEDMODE,3
            brne   SUL4
            ldi    HiLights,Pattern3H
            Idi    LoLights,Pattern3L
            ret
SUL4:       cpi    LEDMODE,4
            brne   SUL5
            ldi    HiLights,Pattern4H
            ldi    LoLights,Pattern4L
            ret
SUL5:       cpi    LEDMODE,5
            brne   SUL6
            ldi    HiLights,Pattern5H
            ldi    LoLights,Pattern5L
            ret
SUL6:       cpi    LEDMODE,6
            brne   SUL7
            ldi    HiLights,Pattern6H
            ldi    LoLights,Pattern6L
            ret
SUL7:       ldi    HiLights,Pattern7H
            ldi    LoLights,Pattern7L
            ret
       StartTimer:      :init TCNT0, TCCR0, TIFR, TTMSK.
            ldi    temp0.0x01      ;div-bv-1 = 0X01
            out    TCNT0,temp0     ;preload the count with a known
val
            out    TCCR0.temp0     ;set to clk/1 mode
            ldi    temp0,0x02
            out    TIFR.temp0      ;force the flag off
            out    TIMSK,temp0     ;enable Timer int
            ldi    FlashCtr, (DutyFlash-1)   ;set up to turn on
LEDs soon
            ret
SaveMode: ;this saves the current LED mode to EE if necessary
            ldi    temp0.1
            out    EEAR.temp0      ;set address
            out    EECR,temp0      ;do read,
            out    EECR.temp0      ;twice
            in     temp0.EEDR      ;grab it
            cp     temp0, LEDMODE  ;same?
            breg   Smret           ;if so, exit
            out    EE DR, LEDMODE  ;put value
;
            ldi    temp0.4         ;compatibility for 8515
            out    EECR,temp0      ;if " " "
            ldi    temp0.2         ;(needed for both 8515 & 1200)
            out    EECR,temp0      ;force write
            nop
SMwait:     sbic   EECR.1          ;break if see LOW
            rimp   SMwait
SMret:      ret
```

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. An apparatus comprising:

a surface;

one or more lights disposed on said surface;

a microprocessor integrally housed in said apparatus and electrically connected to said lights and controlling said lights; and a power source integrally housed in said apparatus and electrically connected to said microprocessor and said lights, wherein said apparatus is portable, self-contained and adapted to be worn by a human being.

2. The apparatus as recited in claim 1, further comprising one or more sound source, wherein said integral power source is electrically connected to said sound source and wherein said microprocessor controls said sound source.

3. The apparatus as recited in claim 1, wherein the surface is a pair of sunglasses or optical glasses.

4. The apparatus as recited in claim 1 wherein the light produced by the one or more lights is white.

5. The apparatus as recited in claim 1, wherein the light produced by the one or more lights is plane polarized.

6. The apparatus as recited in claim 1, wherein the light produced by the one or more lights is varied in color.

7. The apparatus as recited in claim 3, further comprising one or more sound source controlled by said microprocessor.

8. The apparatus as recited in accordance with claim 2, further comprising at least two sound sources.

9. An apparatus for treating learning disorders by selectively stimulating a non-dominant cerebral hemisphere of a patient comprising:

one or more lights positioned in close proximity to a patient's eye;

one or more sound sources positioned in close proximity to a patient's ear;

a microcontroller electrically connected to the lights and the sound sources and controlling the lights and sounds, the one or more lights and sound sources being selectively controlled by the microcontroller; and a power source electrically connected to the microcontroller that provides electricity to the one or more lights, the one or more sound sources and the microcontroller, wherein the lights, sound sources, microcontroller and power source are integral in the apparatus to provide a self-contained, portable apparatus.

10. The apparatus as recited in claim 9, further comprising: a housing in which the lights, sound sources, microcontroller and power source are integrally housed.

11. The apparatus as recited in claim 10, wherein the housing is a pair of sunglasses.

12. The apparatus as recited in according to claim 9, wherein the light produced by the one or more lights is white.

13. The apparatus as recited in claim 9, wherein the light produced by the one or more lights is plane polarized.

14. The apparatus of claim 9, wherein the light produced by the one or more lights is varied in color.

15. The apparatus of claim 9, further comprising at least two sound sources.

16. A method for treating a patient that has been diagnosed with dyslexia, the method comprising the steps of:

identifying a dyslexic patient;

providing a portable, self-contained apparatus to the patient, the apparatus comprising a surface disposable in close proximity to the patient's eyes and ears; one or more light and sound sources disposed on said surface; a microprocessor integrally housed in said apparatus and electrically connected to said light and sound source and controlling said light and sound sources and a power supply integrally housed in said apparatus to provide power to said microprocessor and to said light and sound sources; and selectively stimulating the non-dominant hemisphere of the of the brain of said patient using said apparatus.

17. The method of claim 16, further comprising the steps of stimulating both eyes of a patient.

18. The method of claim 16, wherein the light is defined as being white light.

19. The method of claim 16, wherein the light is plane polarized.

20. The method of claim 16, wherein the light is an LED.

21. The method of claim 16, wherein the patient has been diagnosed with a limbic dysfunction.

22. The method of claim 16, wherein the patient has been diagnosed with Attention Deficit Disorder.

23. The method of claim 16, wherein the patient has been diagnosed with Attention Deficit Hyperactive Disorder.

24. The method of claim 16, wherein the patient has been diagnosed with a behavioral disorder.

25. The method of claim 16, wherein the patient has been diagnosed with learning differences.

26. The method of claim 16, wherein the patient has been diagnosed with a neurological difference caused by hemispheric dominance.

27. The method of claim 16, further comprising the steps of differentially stimulating both eyes and both ears of a patient.

* * * * *

ⓘ

(12) EX PARTE REEXAMINATION CERTIFICATE (9919th)
United States Patent
Jaillet

(10) Number: US 6,443,977 C1
(45) Certificate Issued: Nov. 1, 2013

(54) APPARATUS AND METHOD FOR CHANGING CRITICAL BRAIN ACTIVITY USING LIGHT AND SOUND

(76) Inventor: Peter D. Jaillet, Carrollton, TX (US)

Reexamination Request:
No. 90/012,552, Sep. 13, 2012

Reexamination Certificate for:
Patent No.: 6,443,977
Issued: Sep. 3, 2002
Appl. No.: 09/545,052
Filed: Apr. 7, 2000

Related U.S. Application Data

(63) Continuation-in-part of application No. 09/201,093, filed on Nov. 30, 1998, now Pat. No. 6,299,632.

(51) Int. Cl.
*A61M 21/00* (2006.01)
*A61N 5/06* (2006.01)

(52) U.S. Cl.
USPC .............................................. 607/88; 600/27

(58) Field of Classification Search
None
See application file for complete search history.

(56) References Cited

To view the complete listing of prior art documents cited during the proceeding for Reexamination Control Number 90/012,552, please refer to the USPTO's public Patent Application Information Retrieval (PAIR) system under the Display References tab.

*Primary Examiner* — Deandra Hughes

(57) ABSTRACT

An apparatus and method is disclosed for selectively stimulating cortical brain activity of a patient with hemispheric brain differences using light and/or sound includes exposing the patient to one or more lights (12) placed in close proximity to a patient's eyes (20, 30) wherein the one or more of lights (12) selectively stimulate the non-dominant eye (30) connected to the non-dominant cerebral hemisphere.

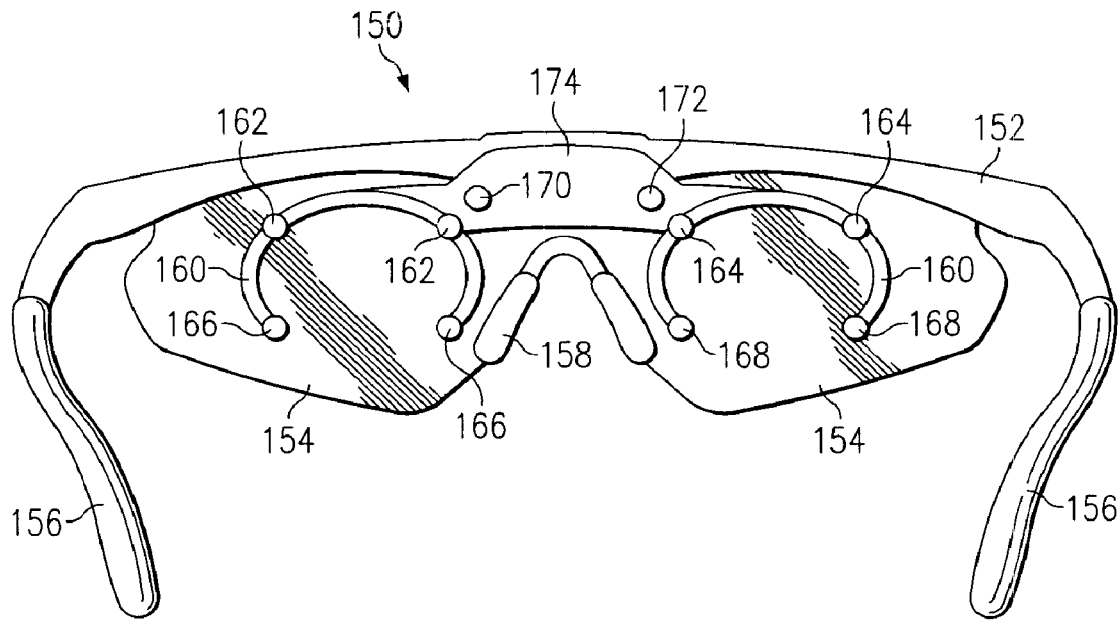

US 6,443,977 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 3 are determined to be patentable as amended.

Claims 4-6, dependent on an amended claim, are determined to be patentable.

New claims 28-57 are added and determined to be patentable.

Claims 2 and 7-27 were not reexamined.

1. An apparatus comprising:
   a lens having a *rear* surface;
   one or more lights disposed on said *rear* surface [and], *wherein all of said lights are* offset from a center portion of said *rear* surface such that said center portion *is in front of an eye of a human being, facing said eye and* is unobstructed;
   a microprocessor integrally housed in said apparatus and electrically connected to said lights and controlling said lights; and
   a power source integrally housed in said apparatus and electrically connected to said microprocessor and said lights, wherein said apparatus is portable, self-contained and adapted to be worn by [a] *said* human being such that said *rear* surface is in close proximity to [and facing an] *said* eye of said human being.

3. The apparatus as recited in claim 1, wherein the [surface] *apparatus* is a pair of sunglasses or optical glasses.

28. *The apparatus as recited in claim 1, further comprising a mode selector switch electrically connected to said microprocessor that controls said one or more lights to selectively stimulate said eye of said human being.*

29. *The apparatus as recited in claim 1, further comprising a mode selector switch electrically connected to said microprocessor that controls said one or more lights to selectively stimulate said eye of said human being at a greater intensity than an other eye of said human being.*

30. *The apparatus as recited in claim 1, wherein said one or more lights comprise one to four lights and each of said one to four lights is directed to a different quadrant of a retina of said human being.*

31. *The apparatus as recited in claim 1, wherein said one or more lights comprise:*
   *one or more first lights directed to a first quadrant of a retina of said human being; and*
   *one or more second lights directed to a second quadrant of said retina of said human being.*

32. *The apparatus as recited in claim 1, wherein said one or more lights comprise:*
   *one or more first lights directed at a first quadrant of a retina of said human being;*
   *one or more second lights directed at a second quadrant of said retina of said human being;*
   *one or more third lights directed at a third quadrant of said retina of said human being; and*
   *one or more fourth lights directed at a fourth quadrant of said retina of said human being.*

33. *The apparatus as recited in claim 1, wherein said lens comprises a first lens, said rear surface comprises a first rear surface, said one or more lights comprise one or more first lights, said center portion comprises a first center portion, said eye comprises a first eye, and said apparatus further comprises:*
   *a second lens having a second rear surface in close proximity to a second eye of said human being;*
   *one or more second lights disposed on said second rear surface and offset from a second center portion of said rear second surface such that said second center portion facing said second eye of said human being is unobstructed;*
   *said microprocessor electrically connected to said second lights and controlling said second lights; and*
   *said power source electrically connected to said second lights.*

34. *The apparatus as recited in claim 33, wherein said one or more first lights consist of a first vertical row of lights, said one or more second lights consist of a second vertical row of lights, and wherein said microprocessor controls said first vertical row of lights and second vertical row of lights to operate together to perform a hemifield stimulation.*

35. *The apparatus as recited in claim 1, wherein said microprocessor pulses said one or more lights in accordance with one or more modes.*

36. *The apparatus as recited in claim 1, wherein said microprocessor controls a duty cycle and an intensity of said one or more lights.*

37. *The apparatus as recited in claim 1, wherein said lens permits a light, a modified light or no light to pass through said lens.*

38. *The apparatus as recited in claim 1, wherein said apparatus comprises a monocle or eye patch.*

39. *An apparatus comprising:*
   *a lens having a front surface and a rear surface, wherein said front surface is unobstructed and said rear surface faces an eye of a human being;*
   *one or more light sources disposed on said rear surface such that none of said one or more light sources are directly in front of said eye of said human being;*
   *a microprocessor integrally housed in said apparatus and electrically connected to said one or more light sources and controlling said one or more light sources;*
   *a power source integrally housed in said apparatus and electrically connected to said microprocessor and said one or more light sources; and*
   *wherein said apparatus is portable, self-contained and adapted to be worn by a human being.*

40. *The apparatus as recited in claim 39, wherein said one or more light sources are offset from a center portion of said rear surface such that said center portion is unobstructed.*

41. *The apparatus as recited in claim 39, further comprising a mode selector switch electrically connected to said microprocessor that controls said one or more light sources to selectively stimulate said eye of said human being.*

42. *The apparatus as recited in claim 39, further comprising a mode selector switch electrically connected to said microprocessor that controls said one or more light sources to selectively stimulate said eye of said human being at a greater intensity than an other eye of said human being.*

43. *The apparatus as recited in claim 39, wherein said one or more light sources comprise one to four light sources and* each of said one to four light sources is directed to a different quadrant of a retina of said human being.

44. The apparatus as recited in claim 39, wherein said one or more light sources comprise:
one or more first light sources directed to a first quadrant of a retina of said human being; and
one or more second light sources directed to a second quadrant of said retina of said human being.

45. The apparatus as recited in claim 39, wherein said one or more light sources comprise:
one or more first light sources directed at a first quadrant of a retina of said human being;
one or more second light sources directed at a second quadrant of said retina of said human being;
one or more third light sources directed at a third quadrant of said retina of said human being; and
one or more fourth light sources directed at a fourth quadrant of said retina of said human being.

46. The apparatus as recited in claim 39, wherein said lens comprises a first lens, said front surface comprises a first front surface, said rear surface comprises a first rear surface, said one or more light sources comprise one or more first light sources, said eye comprises a first eye, and said apparatus further comprises:
a second lens having a second front surface and a second rear surface, wherein said second front surface is unobstructed and said second rear surfaces faces a second eye of said human being;
one or more second light sources disposed on said second rear surface such that said one or more light sources are not directly in front of said second eye of said human being;
said microprocessor electrically connected to said one or more second light sources and controlling said one or more second light sources; and
said power source electrically connected to said one or more second light sources.

47. The apparatus as recited in claim 46, wherein said one or more first light sources consist of a first vertical row of light sources, said one or more second light sources consist of a second vertical row of light sources, and wherein said microprocessor controls said first vertical row of light sources and second vertical row of light sources to operate together to perform a hemifield stimulation.

48. The apparatus as recited in claim 39, wherein said microprocessor pulses said one or more light sources in accordance with one or more modes.

49. The apparatus as recited in claim 39, wherein said microprocessor controls a duty cycle and an intensity of said one or more light sources.

50. The apparatus as recited in claim 39, wherein said lens permits a light, a modified light or no light to pass through said lens.

51. The apparatus as recited in claim 39, wherein said apparatus comprises a monocle or eye patch.

52. The apparatus as recited in claim 39, further comprising one or more sound sources, wherein said integral power source is electrically connected to said one or more sound sources and said microprocessor controls said one or more sound sources.

53. The apparatus as recited in claim 39, wherein said apparatus comprises a pair of sunglasses or optical glasses.

54. The apparatus as recited in claim 39, wherein said one or more light sources produce a white light.

55. The apparatus as recited in claim 39, wherein said one or more light sources produce a plane polarized light.

56. The apparatus as recited in claim 39, wherein said one or more light sources produce a colored light.

57. The apparatus as recited in claim 39, wherein said one or more light sources produce a multicolored light.

\* \* \* \* \*